United States Patent
Stevenson et al.

(10) Patent No.: US 8,119,551 B2
(45) Date of Patent: Feb. 21, 2012

(54) ZEOLITE CATALYST WITH DEPOSITED GERMANIUM, ALUMINUM AND PLATINUM FOR AROMATIZATION OF ALKANES, PROCESS OF MAKING AND PROCESS OF USING THEREOF

(75) Inventors: Scott Stevenson, Houston, TX (US); Gopalakrishnam G. Juttu, Glen Mills, PA (US); Michael Mier, Waller, TX (US); Robin J. Bates, Pearland, TX (US); Dustin Farmer, Houston, TX (US); Scott Mitchell, The Woodlands, TX (US); Alla K. Khanmamedova, Sugar Land, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 158 days.

(21) Appl. No.: 12/657,158

(22) Filed: Jan. 14, 2010

(65) Prior Publication Data
US 2011/0172479 A1 Jul. 14, 2011

(51) Int. Cl.
*B01J 29/06* (2006.01)

(52) U.S. Cl. ............... 502/60; 502/63; 502/34; 502/66; 502/71; 502/74; 502/77

(58) Field of Classification Search ............... 502/60, 502/63, 64, 66, 71, 74, 77
See application file for complete search history.

(56) References Cited

U.S. PATENT DOCUMENTS
5,227,557 A   7/1993   Bournonville et al.
5,456,822 A   10/1995   Marcilly et al.

*Primary Examiner* — Elizabeth Wood
(74) *Attorney, Agent, or Firm* — Cantor Colburn LLP

(57) ABSTRACT

The present invention is for a catalyst, a process for making the catalyst and a process for using the catalyst in aromatization of alkanes having three to five carbon atoms per molecule, such as propane, to aromatics, such as benzene, toluene and xylene. The catalyst is an aluminum-silicon zeolite having a silicon to aluminum atomic ratio (Si:Al) greater than 15:1, such as MFI or ZSM-5, on which germanium, aluminum and a noble metal, such as platinum, have been deposited. The catalyst may be bound with magnesia, alumina, titania, zirconia, thoria, silica, boria or mixtures thereof. The aluminum and germanium may be deposited simultaneously on the zeolite.

19 Claims, 1 Drawing Sheet

Activity test result for Pt-Ge-Al/H-ZSM-5 catalyst 317-062-4Pt.

Pt-Ge-Al/H-ZSM-5 catalyst performed better selectivity and better activity stability in comparison with Pt-Ge/H-ZSM-5 catalyst.

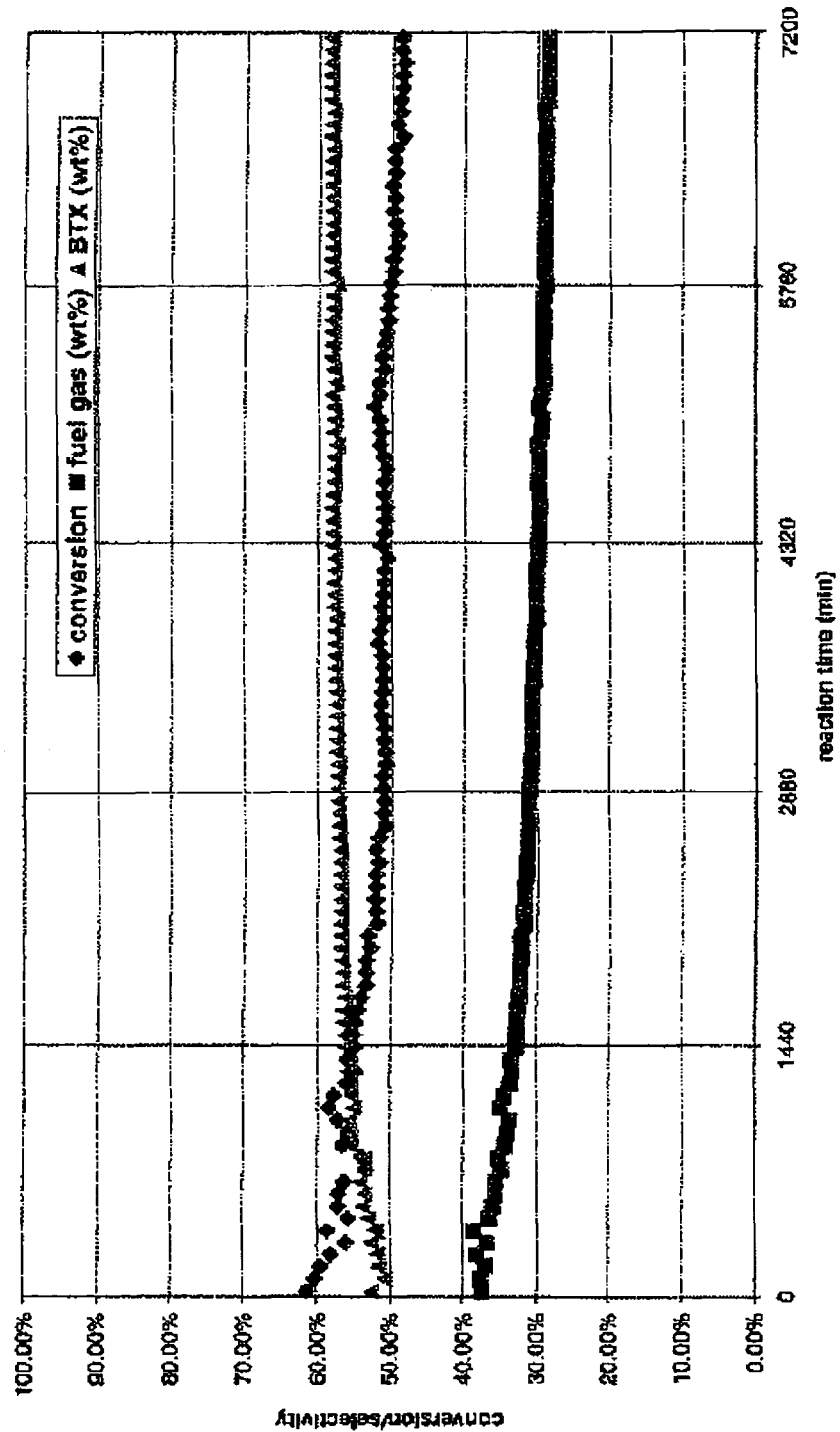
Figure 1. Activity test result for Pt-Ge-Al/H-ZSM-5 catalyst 317-062-4Pt.
Pt-Ge-Al/H-ZSM-5 catalyst performed better selectivity and better activity stability in comparison with Pt-Ge/H-ZSM-5 catalyst.

ZEOLITE CATALYST WITH DEPOSITED GERMANIUM, ALUMINUM AND PLATINUM FOR AROMATIZATION OF ALKANES, PROCESS OF MAKING AND PROCESS OF USING THEREOF

BACKGROUND OF THE INVENTION

1. Field of the Invention

This invention relates to a zeolite catalyst, such as a MFI, L or β zeolite on which platinum, germanium and aluminum have been deposited. One use of this zeolite catalyst is for conversion of aliphatic hydrocarbons, such as propane, to aromatic hydrocarbons, such as benzene, toluene and xylenes.

2. Description of the Prior Art

Zeolite is a crystalline hydrated aluminosilicate that may contain other metals in the framework of the zeolite crystal or deposited, exchanged or impregnated onto the zeolite. A method for preparing a zeolite comprises (a) preparing an aqueous mixture of silicon oxide and sources of oxides of aluminum; and (b) maintaining said aqueous mixture under crystallization conditions until crystals of zeolite form. Zeolite by itself is known as an operative catalyst for many hydrocarbon conversion reactions but selectivity to a particular product may be low. Much zeolite research has focused on modifying the zeolite by depositing particular elements or compounds on the surface of the zeolite.

U.S. Pat. No. 5,456,822 discloses an MFI zeolite in hydrogen form with silicon, aluminum and/or gallium in the framework; a matrix of a refractory oxide and at least one oxide of magnesium, aluminum, titanium, zirconium, thorium, silicon or boron; gallium; platinum and at least one other metal, such as tin, germanium, indium, copper, iron, molybdenum, gallium, thallium, gold, silver, ruthenium, chromium, tungsten and lead, as a catalyst for aromatization of hydrocarbons of two to nine carbon atoms per molecule.

U.S. Pat. No. 5,227,557 discloses an MFI zeolite with platinum and at least one metal of tin, germanium, lead and indium, optionally containing an amorphous matrix, as a catalyst for aromatization of hydrocarbons of two to four carbon atoms per molecule.

SUMMARY OF THE INVENTION

In a process for aromatization of a feed comprising alkanes having three to five carbon atoms per molecule a catalyst comprising a zeolite having a silicon:aluminum ratio greater than about 15:1; germanium deposited on the zeolite in the range from about 0.1 to about 3.0 weight percent; aluminum deposited on the zeolite in the range of Ge:Al mole ratio from about 0.02 to about 7.5; and a noble metal deposited on the zeolite is contacted with at least one alkane at aromatization conditions and the aromatic product is recovered.

The catalyst is a zeolite aluminosilicate on which germanium, aluminum and platinum are deposited in the amounts and ranges above. The catalyst is synthesized by depositing germanium, aluminum and a noble metal, such as platinum, on a zeolite in the amounts and ranges above. Germanium and aluminum may be deposited simultaneously. The zeolite may be calcined after deposition. Examples of the zeolite structure are MFI, L and β. A specific example of the zeolite structure is MFI or ZSM-5. The zeolite contains aluminum, silicon and, optionally, another element in the framework.

BRIEF DESCRIPTION OF THE DRAWINGS

A more complete appreciation of the invention and many of the attendant advantages thereof will be readily understood by reference to the following detailed description when considered in connection with the accompanying drawings:

FIG. 1 is a graph of propane conversion, fuel gas selectivity and BTX selectivity for a reaction for aromatization of propane (Example 4).

DETAILED DESCRIPTION OF THE INVENTION

Platinum, germanium and aluminum are deposited on a zeolite. The zeolite can be prepared by any known method of preparing a zeolite structure of aluminum, silicon and, optionally, other elements, such as gallium, germanium, tin, boron, titanium and iron. Zeolites are known to be crystallized silicates and include structures of $TO_4$ tetrahedra, which form a three dimensional network by sharing oxygen atoms where T represents tetravalent silicon and trivalent aluminum. Other trivalent elements may be substituted for the aluminum and other tetravalent elements may be substituted for the silicon. In one embodiment of the invention the zeolite consists essentially of silicon and aluminum.

Zeolites generally crystallize from an aqueous solution. The typical technique for synthesizing zeolites comprises converting an amorphous gel to zeolite crystals by a hydrothermal process, employing a dissolution/recrystallization mechanism. The reaction medium may also contain structuring agents which are incorporated in the microporous space of the zeolite network during crystallization, thus controlling the construction of the network and assisting to stabilize the structure through the interactions with the zeolite components.

In the present invention, the as synthesized silicon to aluminum atomic ratio (Si:Al) of the zeolite is greater than 15:1 or in the range from 35:1 to 300:1. Platinum, germanium and aluminum are deposited on the zeolite by any known method of depositing a metal on a zeolite. Typical methods of depositing a metal on zeolite are ion exchange and impregnation, such as by incipient wetness. Platinum is present in the range of from 0.15% to 1.0% by weight, germanium is present in the range from 0.1% to 3.0% by weight, from 0.1% to 2.0% by weight or from 0.15% to 0.6% by weight and the deposited aluminum is present at a Ge:Al molar ratio in the range from 0.02 to 7.5 or in the range from 0.08 to 0.35 or is present in the range from about 0.15 to about 2.0 weight percent.

The catalyst may be bound by oxides of magnesium, aluminum, titanium, zirconium, thorium, silicon, boron and mixtures thereof. In one embodiment, the support is an oxide of silicon (silica).

The invention having been generally described, the following examples are given as particular embodiments of the invention and to demonstrate the practice and advantages thereof. It is understood that the examples are given by way of illustration and are not intended to limit the specification or the claims to follow in any manner.

ZSM-5 zeolite of $Si/Al_2$ ratio of 100 was prepared by standard procedures. Zeolite powder was ion-exchanged with ammonia to remove sodium ions and converted to $H^+$ form by calcination at 550° C. for ten hours. Pt—Ge—Al/H-ZSM-5 catalyst was prepared by impregnating H-ZSM-5 zeolite with germanium and aluminum by incipient wetness, calcining at 600° C. for ten (10) hours, binding with silica at a ratio of 1:1 by weight, calcining at 550° C. for ten (10) hours, crushing and sieving to 20/40 mesh size, depositing platinum by ion exchange or impregnation and calcining at 300° C. for about three (3) to twenty (20) hours. The catalyst was used in a reaction of propane dehydrocyclodimerization at a pressure of 22 psig and a WHSV of 1.0 $hr^{-1}$ for a run time of about eight hours for each sample at a temperature as indicated in Table 1. Examples were repeated for different amounts of Ge, Al and Pt at these conditions with the results indicated in Table 1.

Examples were repeated for different amounts of Al with the amounts of Ge and Pt constant at the conditions indicated above with the results indicated in Table 2. Examples were repeated for a zeolite with Si/Al ratio of 30 and different amounts of Ge with the amounts of Al and Pt constant at the conditions indicated above with the results indicated in Table 3. Platinum was ion exchanged. Examples were repeated for a zeolite with Si/Al ratio of 30 and different amounts of Ge with the amounts of Al and Pt constant at the conditions indicated above with the results indicated in Table 4. Platinum was impregnated (incipient wetness). The propane conversion, fuel gas selectivity and benzene, toluene, xylenes (BTX) selectivity for Example 4 are shown in FIG. 1.

TABLE 1

| Zeolite | Si (wt %) | Al (wt %) | Si/Al (zeolite) (mole ratio) | Ge depos. (wt %) | Al depos. (wt %) | Si/Ge (mole ratio) | Si/Al total (mole ratio) | Ge/Al depos. (mole ratio) | Conv (%) | Temp. (° C.) | Fuel gas Sel | BTX Sel. |
|---|---|---|---|---|---|---|---|---|---|---|---|---|
| 317-048 (CE1) | 46.73 | 0.83 | 54.29 | 0 | 0 | — | 54.29 | — | | | | |
| 309-086-4 (CE2) | 44.67 | 0.83 | 51.90 | 0.30 | 0 | 386.13 | 51.90 | — | 50 | 482 | 39 | 48 |
| 309-086-3 (CE3) | 44.84 | 0.82 | 52.73 | 0.59 | 0 | 197.08 | 52.73 | — | 50 | 485 | 40 | 47 |
| 309-086-2 (CE4) | 44.91 | 0.83 | 52.18 | 0.89 | 0 | 130.86 | 52.18 | — | 50 | 485 | 40 | 47 |
| 309-086-1 (CE5) | 44.17 | 0.83 | 51.32 | 1.16 | 0 | 98.74 | 51.32 | — | 50 | 485 | 40 | 47 |
| 309-086-6 (CE6) | 44.62 | 0.84 | 51.22 | 1.68 | 0 | 68.87 | 51.22 | — | 50 | 495 | 38 | 46 |
| 309-086-5 (Ex1) | 44.09 | 1.33 | 52.73 | 0.57 | 0.51 | 200.59 | 31.97 | 0.416 | 50 | 483 | 38 | 52 |

TABLE 2

| Zeolite | Si (wt %) | Al (wt %) | Si/Al (zeolite) (mole ratio) | Ge depos. (wt %) | Al depos. (wt %) | Si/Ge (mole ratio) | Si/Al total (mole ratio) | Ge/Al depos. (mole ratio) | Conv (%) | Temp. (° C.) | Fuel gas Sel | BTX Sel. |
|---|---|---|---|---|---|---|---|---|---|---|---|---|
| 317-036 (CE7) | 44.07 | 0.78 | 54.48 | 0 | 0 | — | 54.48 | — | | | | |
| 317-062-1 (CE8) | 44.70 | 0.80 | 53.87 | 0.61 | 0 | 190.02 | 53.87 | — | 50 | 473 | 51.5 | 35 |
| 317-062-2 (Ex2) | 43.91 | 1.32 | ~54 | 0.59 | 0.52 | 193.00 | 32.08 | 0.42 | 50 | 477 | 46.0 | 39 |
| 317-062-3 (Ex3) | 43.86 | 1.87 | ~54 | 0.60 | 1.07 | 189.56 | 22.62 | 0.21 | 50 | 482 | 44.0 | 42 |
| 317-062-4 (Ex4) | 43.30 | 2.30 | ~54 | 0.58 | 1.50 | 193.60 | 18.15 | 0.14 | 50 | 486 | 36.0 | 51 |

TABLE 3

| Zeolite | Si (wt %) | Al (wt %) | Si/Al (zeolite) (mole ratio) | Ge depos. (wt %) | Al depos. (wt %) | Si/Ge (mole ratio) | Si/Al total (mole ratio) | Ge/Al depos. (mole ratio) | Conv (%) | Temp. (° C.) | Fuel gas Sel | BTX Sel. |
|---|---|---|---|---|---|---|---|---|---|---|---|---|
| H-ZSM-5 CBV3020E (CE9) | 41.47 | 2.41 | 16.59 | 0 | 0 | — | 16.59 | — | | | | |
| 317-132-Al-1 (Ex5) | 42.47 | 3.08 | 16.59 | 0.94 | 0.67 | 117.16 | 13.29 | 0.52 | — | — | — | — |
| 317-132-Al-2 (Ex6) | 42.20 | 3.14 | 16.59 | 1.93 | 0.73 | 56.70 | 12.96 | 0.98 | 70 | 508 | 51 | 42 |
| 317-132-Al-3 (Ex7) | 41.62 | 3.02 | 16.59 | 2.82 | 0.61 | 38.27 | 13.29 | 1.72 | 70 | 546 | 47 | 45 |

TABLE 4

| Catalyst | Si (wt %) | Al (wt %) | Si/Al zeolite (mole ratio) | Ge depos. (wt %) | Al depos. (wt %) | Si/Ge (mole ratio) | Si/Al total (mole ratio) | Ge/Al depos. (mole ratio) | Conv (%) | Temp. (° C.) | Fuel gas Sel (%) | BTX Sel. (%) |
|---|---|---|---|---|---|---|---|---|---|---|---|---|
| 317-132-Al-1-Pt-2 (Ex8) | 42.47 | 3.08 | 16.59 | 0.94 | 0.67 | 117.16 | 13.29 | 0.52 | 70 | 507 | 59 | 34 |
| 317-132-Al-2-Pt-2 (Ex9) | 42.20 | 3.14 | 16.59 | 1.93 | 0.73 | 56.70 | 12.96 | 0.98 | 50 | 526 | 45 | 42 |
| 317-132-Al-3-Pt-2 (Ex10) | 41.62 | 3.02 | 16.59 | 2.82 | 0.61 | 38.27 | 13.29 | 1.72 | 50 | 556 | 36 | 50 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for making a catalyst comprising:
    a) depositing germanium in the range from about 0.1 to about 3.0 weight percent on a zeolite having a silicon:aluminum ratio greater than about 15:1;
    b) depositing aluminum on the zeolite in the range of Ge:Al mole ratio from about 0.02 to about 7.5; and
    c) depositing a noble metal on the zeolite
    wherein the germanium and aluminum are deposited simultaneously on the zeolite.
2. The process of claim 1 wherein the zeolite is MFI.
3. The process of claim 1 wherein the noble metal is platinum.
4. The process of claim 1 wherein the silicon:aluminum ratio is about 35:1 to 300:1.
5. The process of claim 3 wherein platinum is present in the range of from 0.15% to 1.0% by weight.
6. The process of claim 1 wherein germanium is present in the range from 0.1% to 3.0% by weight.
7. The process of claim 1 wherein germanium is present in the range from 0.1% to 2.0% by weight.
8. The process of claim 1 wherein the Ge:Al molar ratio is in the range from 0.08 to 0.35.
9. The process of claim 1 wherein the aluminum is deposited on the zeolite in the range from about 0.15 to about 2.0 weight percent.
10. The process of claim 1 further comprising binding the catalyst with oxides of magnesium, aluminum, titanium, zirconium, thorium, silicon, boron or mixtures thereof.
11. The process of claim 1 further comprising binding the catalyst with oxides of silicon (silica).
12. A catalyst comprising:
    a) a zeolite having a silicon:aluminum ratio greater than about 15:1;
    b) germanium deposited on the zeolite in the range from about 0.1 to about 3.0 weight percent;
    c) aluminum deposited on the zeolite in the range of Ge:Al mole ratio from about 0.02 to about 7.5; and
    d) a noble metal deposited on the zeolite.
13. The catalyst of claim 12 wherein the zeolite is MFI.
14. The catalyst of claim 12 wherein the noble metal is platinum.
15. The catalyst of claim 12 wherein the silicon:aluminum ratio is about 35:1 to 300:1.
16. The catalyst of claim 14 wherein platinum is present in the range of from 0.15% to 1.0% by weight.
17. The catalyst of claim 12 wherein germanium is present in the range from 0.1% to 2.0% by weight.
18. The catalyst of claim 12 where in germanium is present in the range from 0.15% to 0.6% by weight.
19. The catalyst of claim 12 wherein the Ge:Al molar ratio is in the range from 0.08 to 0.35.

* * * * *